United States Patent
Chang et al.

(10) Patent No.: US 9,901,304 B2
(45) Date of Patent: Feb. 27, 2018

(54) ANALYSIS PROCESS DEVICE

(71) Applicant: Winbond Electronics Corp., Taichung (TW)

(72) Inventors: Chia-Chi Chang, Taipei (TW); Chung-Yu Wu, Hsinchu (TW)

(73) Assignee: WINBOND ELECTRONICS CORP., Taichung (TW)

( * ) Notice: Subject to any disclaimer, the term of this patent is extended or adjusted under 35 U.S.C. 154(b) by 218 days.

(21) Appl. No.: 14/724,231

(22) Filed: May 28, 2015

(65) Prior Publication Data

US 2016/0249861 A1    Sep. 1, 2016

(30) Foreign Application Priority Data

Feb. 26, 2015  (TW) .............................. 104106172 A (51) Int. Cl.
*A61B 5/02*   (2006.01)
*A61B 5/00*   (2006.01)
*A61B 5/024*  (2006.01)

(52) U.S. Cl.
CPC .......... *A61B 5/7203* (2013.01); *A61B 5/7246* (2013.01); *A61B 5/7264* (2013.01); *A61B 5/7278* (2013.01); *A61B 5/02* (2013.01); *A61B 5/02416* (2013.01); *A61B 2562/0219* (2013.01)

(58) Field of Classification Search
USPC ....................................................... 600/477
See application file for complete search history.

(56) References Cited

U.S. PATENT DOCUMENTS

| | | | |
|---|---|---|---|
| 7,499,686 | B2 | 3/2009 | Sinclair et al. |
| 2006/0122525 | A1* | 6/2006 | Shusterman ....... A61B 5/04007 600/513 |
| 2011/0054290 | A1* | 3/2011 | Derchak .............. A61B 5/0002 600/388 |
| 2014/0064527 | A1 | 3/2014 | Walther et al. |

FOREIGN PATENT DOCUMENTS

TW            308533 B       6/1997

* cited by examiner

*Primary Examiner* — Nicole F Johnson
(74) *Attorney, Agent, or Firm* — Muncy, Geissler, Olds & Lowe, P.C.

(57) ABSTRACT

An analysis process device processing a first physiological signal to generate an analysis result and including a sensing unit, a separation unit, a comparing unit, and a reconstruction unit is provided. The sensing unit detects the first physiological signal to generate a sensing signal. The separation unit separates the sensing signal to generate a plurality of intrinsic characteristic signals. The comparing unit compares each of the intrinsic characteristic signals with a reference signal and generates a plurality of comparing results. The reconstruction unit divides the intrinsic characteristic signals into a first group and a second group according to the comparing results and generates the analysis result according to the intrinsic characteristic signals of the first group.

19 Claims, 6 Drawing Sheets

ANALYSIS PROCESS DEVICE

CROSS REFERENCE TO RELATED APPLICATIONS

This Application claims priority of Taiwan Patent Application No. 104106172, filed on Feb. 26, 2015, the entirety of which is incorporated by reference herein.

BACKGROUND OF THE INVENTION

Field of the Invention

The invention relates to an analysis process device, and more particularly to an analysis process device for physiological signals.

Description of the Related Art

As technology develops, many medical apparatuses are not only providing original medical operations, but they also have remote-control and monitoring operations. Additionally, many mobile medical apparatuses such as wearable monitoring devices have gradually appeared on the market. However, physiological signals from the human body are non-stable and non-linear signals. If physiological signals are analyzed by conventional methods, medical workers may make errors in their estimations based on conventional analyses.

BRIEF SUMMARY OF THE INVENTION

In accordance with an embodiment, an analysis process device processes a first physiological signal to generate an analysis result and comprises a sensing unit, a separation unit, a comparing unit, and a reconstruction unit. The sensing unit detects the first physiological signal to generate a sensing signal. The separation unit separates the sensing signal to generate a plurality of intrinsic characteristic signals. The comparing unit compares each of the intrinsic characteristic signals with a reference signal and generates a plurality of comparing results. The reconstruction unit divides the intrinsic characteristic signals into a first group and a second group according to the comparing results and generates the analysis result according to the intrinsic characteristic signals of the first group.

In accordance with a further embodiment, an analysis method to analyze a first physiological signal and generate an analysis result comprises sensing the first physiological signal to generate a sensing signal; separating the sensing signal to generate a plurality of intrinsic characteristic signals; comparing each of the intrinsic characteristic signals with a reference signal to generate a comparing result; and dividing the intrinsic characteristic signals into a first group and a second group according to the comparing results and generating the analysis result according to the intrinsic characteristic signals of the first group.

A detailed description is given in the following embodiments with reference to the accompanying drawings.

BRIEF DESCRIPTION OF THE DRAWINGS

The invention can be more fully understood by referring to the following detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
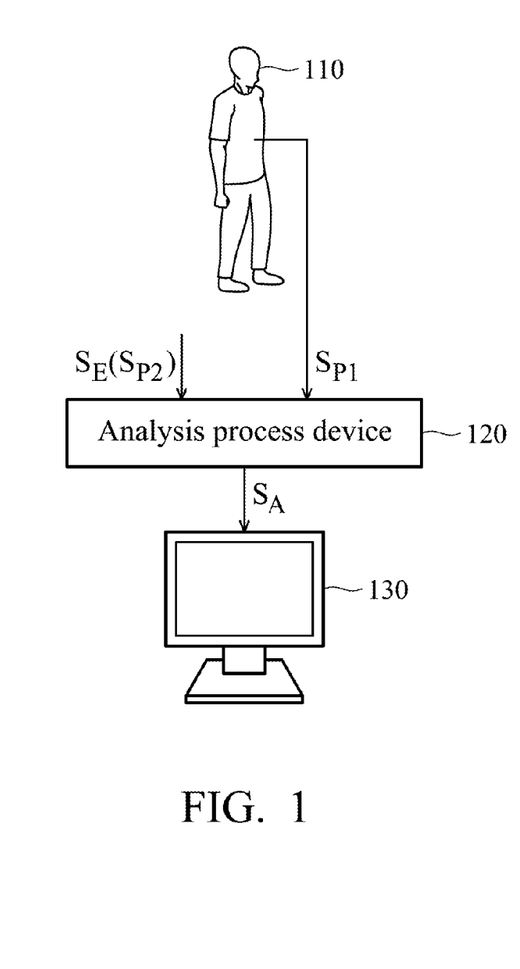
FIG. 1 is a schematic diagram of an exemplary embodiment of an analysis process device, in accordance with an embodiment of the invention.

FIG. 1 is a schematic diagram of an exemplary embodiment of an analysis process device, in accordance with an embodiment of the invention. The analysis process device 120 generates an analysis result $S_A$ according to a physiological signal $S_{P1}$ generated from a human 110 and an external signal $S_E$. A user, such as a medical worker, can determine the physiological condition of the human 110 according to the analysis result $S_A$. In one embodiment, a display device 130 displays an image or text to represent the analysis result $S_A$. The user obtains the physiological conditions of the human 110 according to the displayed image or text.

The invention does not limit the kind of physiological signal $S_{P1}$. Any signal measured from the human 110 can be used as the physiological signal $S_{P1}$. For example, the physiological signal $S_{P1}$ is a pulse rate, a blood pressure, a heartbeat, and so on. Additionally, the invention does not limit the kind of external signal $S_E$. In one embodiment, the external signal $S_E$ is another physiological signal $S_{P2}$ of the human 110. For example, if the physiological signal $S_{P1}$ is the blood pressure of the human 110, since the measure of the blood pressure is influenced by the breathing of the human 110, the external signal $S_E$ is a breathing signal of the human 110. In another embodiment, assuming that the physiological signal $S_{P1}$ is the pulse rate of the human 110. After taking a strenuous exercise, the pulse rate of the human 110 is influenced. Therefore, in this case, the external signal $S_E$ is a signal relating to the shaking of the human 110.

In this embodiment, since the physiological signal $S_{P1}$ is influenced by the external signal $S_E$, the analysis process device 120 detects the external signal $S_E$ to cancel a component of the physiological signal $S_{P1}$, wherein the component is influenced by the external signal $S_E$. In one embodiment, the analysis process device 120 separates the physiological signal $S_{P1}$ to generate a plurality of intrinsic characteristic signals and then compares each of the intrinsic characteristic signals with the external signal $S_E$ to find the component influenced by the external signal $S_E$ and then reconstructs the un-influenced components to generate a clean analysis result. Since the reconstructed components are not influenced by the external signal $S_E$, the user is capable of utilizing the analysis result having clean components to make a correct decision.

Figure 2:
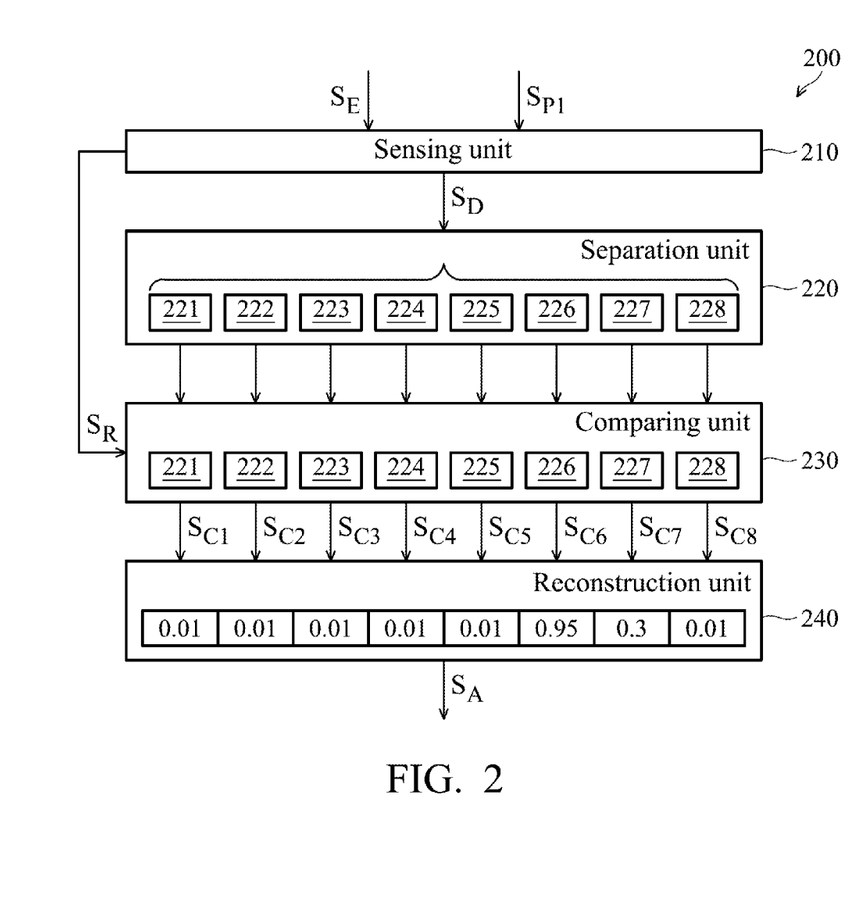
FIG. 2 is another schematic diagram of an exemplary embodiment of an analysis process device, in accordance with an embodiment of the invention.

FIG. 2 is another schematic diagram of an exemplary embodiment of an analysis process device, in accordance with an embodiment of the invention. The analysis process device 200 comprises a sensing unit 210, a separation unit 220, a comparing unit 230, and a reconstruction unit 240. The sensing unit 210 senses the physiological signal $S_{P1}$ to generate a sensing signal $S_D$ and senses the external signal $S_E$ to generate a reference signal $S_R$.

The invention does not limit the kind of sensing unit 210. Any sensing element can be applied in the sensing unit 210, as long as the element is capable of sensing the physiological conditions of a human. In one embodiment, the sensing unit 210 comprises at least a force sensor, a piezoelectric sensor, an accelerator, a wearable sensor, a photoplethysmo-sensor, or a flexibility sensor.

In another embodiment, the sensing unit 210 comprises two sensing elements to sense the physiological signal $S_{P1}$ and the external signal $S_E$ respectively. In other embodiments, the physiological signal $S_{P1}$ and the external signal $S_E$ are sensed by the same element.

Figure 3A:
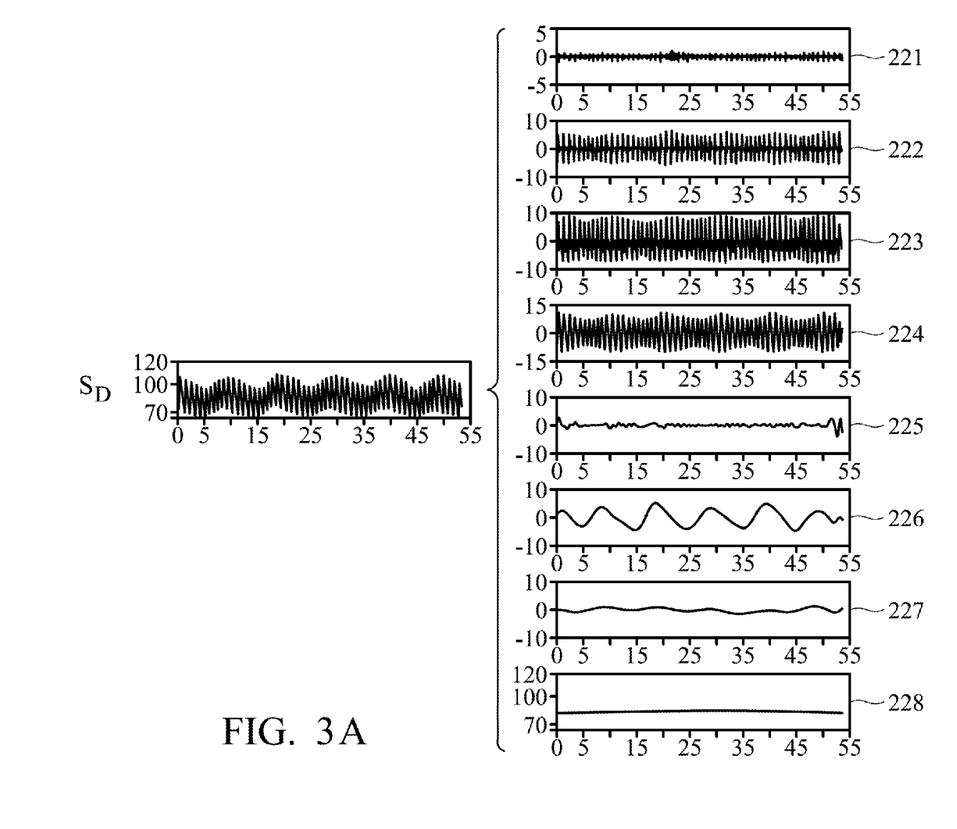
FIG. 3A is a schematic diagram of an exemplary embodiment of the relationship between the sensing signal $S_D$ and the intrinsic characteristic signals 221~228, in accordance with an embodiment of the invention.

The separation unit 220 separates the sensing signal $S_D$ to generate the intrinsic characteristic signals 221~228. FIG. 3A is a schematic diagram of an exemplary embodiment of the relationship between the sensing signal $S_D$ and the intrinsic characteristic signals 221~228, in accordance with an embodiment of the invention. The separation unit 220 generates the intrinsic characteristic signals 221~228 according to the sensing signal $S_D$, but the disclosure is not limited thereto. The number of intrinsic characteristic signals is not limited. In some embodiments, the number of intrinsic characteristic signals generated by the separation unit 220 is any number.

In one embodiment, when the intrinsic characteristic signals 221~228 are overlapped to generate an overlap result, the overlap result is the same as the sensing signal $S_D$. Therefore, the separation unit 220 utilizes a non-distortion method to separate the sensing signal $S_D$. The invention does not limit how the separation unit 220 separates the sensing signal $S_D$. In one embodiment, the separation unit 220 utilizes an empirical mode decomposition (EMD) method to separate the sensing signal $S_D$ from high frequency to low frequency.

Figure 3B:
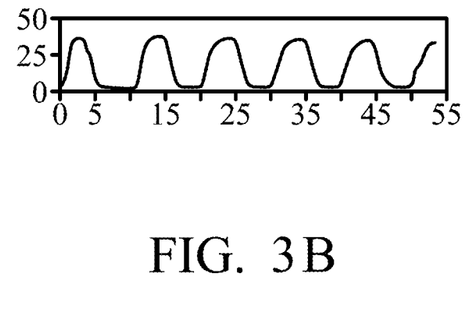
FIG. 3B is a schematic diagram of an exemplary embodiment of a reference signal, in accordance with an embodiment of the invention.

The comparing unit 230 compares each of the intrinsic characteristic signals 221~228 with the reference signal $S_R$ to generate comparing results $S_{C1}$~$S_{C8}$. In one embodiment, the comparing results $S_{C1}$~$S_{C8}$ mean similarities between the intrinsic characteristic signals 221~228 and the reference signal $S_R$. FIG. 3B is a schematic diagram of an exemplary embodiment of a reference signal, in accordance with an embodiment of the invention. In this embodiment, the reference signal $S_R$ is a physiological signal, such as a breathing signal. Refer to FIGS. 3A and 3B, the reference signal $S_R$ is the same as the intrinsic characteristic signal 226. Therefore, the value of the comparing result $S_{C6}$ generated by the comparing unit 230 is a maximum value (e.g. 0.95) higher than each of comparing results $S_{C1}$~$S_{C5}$ and $S_{C7}$~$S_{C8}$.

The invention does not limit how the comparing unit 230 receives and outputs signals. In one embodiment, the comparing unit 230 utilizes a serial method or a parallel method to receive the intrinsic characteristic signals 221~228 and output the comparing results $S_{C1}$~$S_{C8}$. In another embodiment, the method of receiving signals is different from the method of outputting signals. For example, the comparing unit 230 utilizes a serial method or a parallel method to receive the intrinsic characteristic signals 221~228 and utilizes the parallel method or the serial method to output the comparing results $S_{C1}$~$S_{C8}$.

The reconstruction unit 240 divides the intrinsic characteristic signals 221~228 into a first group and a second group according to the comparing result $S_{C1}$~$S_{C8}$. In one embodiment, the comparing results $S_{C1}$~$S_{C8}$ are utilized to obtain similarities between the intrinsic characteristic signals 221~228 and the reference signal $S_R$. The reconstruction unit 240 classifies at least one intrinsic characteristic signal into the first group and classifies the other intrinsic characteristic signals into the second group, wherein the similarity between the intrinsic characteristic signal in the first group and the reference signal $S_R$ is less than a pre-determined value and the similarities between the intrinsic characteristic signals in the second group and the reference signal $S_R$ is higher than the pre-determined value. In one embodiment, the reconstruction unit 240 classifies the intrinsic characteristic signals 221~225 and 227~228 into the first group and classifies the intrinsic characteristic signal 226 into the second group.

Since the similarities between the intrinsic characteristic signals 221~225 and 227~228 in the second group and the reference signal $S_R$ is low, it means that the intrinsic characteristic signals 221~225 and 227~228 are not influenced by the external signal $S_E$. Therefore, the reconstruction unit 240 generates an analysis result $S_A$ according to the intrinsic characteristic signals 221~225 and 227~228 in the first group. In one embodiment, the reconstruction unit 240 directly provides one of the intrinsic characteristic signals 221~225 and 227~228 as the analysis result $S_A$. In another embodiment, the reconstruction unit 240 reconstructs the intrinsic characteristic signals 221~225 and 227~228 to generate the analysis result $S_A$. The invention does not limit how the reconstruction unit 240 receives the comparing result $S_{C1}$~$S_{C8}$. In one embodiment, the reconstruction unit 240 utilizes a serial method or a parallel method to receive the comparing result $S_{C1}$~$S_{C8}$.

Figure 4:
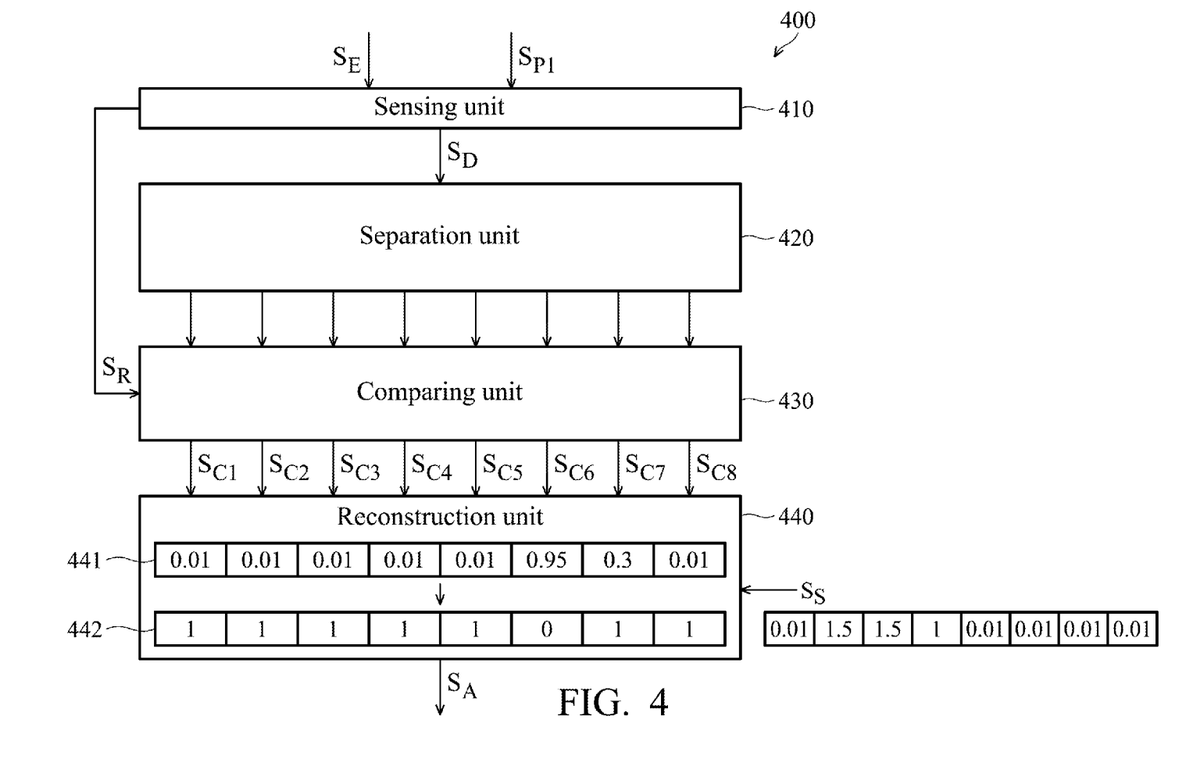
FIG. 4 is a schematic diagram of an exemplary embodiment of an analysis process device, in accordance with an embodiment of the invention.

FIG. 4 is a schematic diagram of an exemplary embodiment of an analysis process device, in accordance with an embodiment of the invention. FIG. 4 is similar to FIG. 2 with the exception that the reconstruction unit 440 enhances the intrinsic characteristic signals 221~225 and 227~228 to generate a plurality of enhancing signals according to a setting value $S_S$ and then generates the analysis result $S_A$ according to the enhancing signals. Since the operation of the sensing unit 410, the separation unit 420 and the comparing unit 430 in FIG. 4 are the same as that of the sensing unit 210, the separation unit 220 and the comparing unit 230 in FIG. 2, the descriptions of the sensing unit 410, the separation unit 420 and the comparing unit 430 in FIG. 4 are omitted.

As shown in FIG. 4, the setting value $S_S$ has a plurality of enhancing components. The reconstruction unit 440 enhances the comparing result $S_{C1}$~$S_{C8}$ according to the enhancing components. In this embodiment, the reconstruction unit 440 converts the similarities 441 between the intrinsic characteristic signals 221~228 and the reference signal $S_R$ to a reconstruction matrix 442, generates a product by multiplying reconstruction matrix 442 by the setting value $S_S$, and then generates the analysis result $S_A$ according to the product.

In one embodiment, one enhancing component of the setting value $S_S$ is different from or the same as another enhancing component of the setting value $S_S$. The invention does not limit how the reconstruction unit 440 receives the comparing results $S_{C1}$~$S_{C8}$ and the setting value $S_S$. In one embodiment, the reconstruction unit 440 utilizes a serial method or a parallel method to receive the comparing results $S_{C1} \sim S_{C8}$. In another embodiment, when the setting value $S_S$ has various enhancing components, the reconstruction unit 440 may utilize a serial method or a parallel method to receive the enhancing components. In other embodiment, the setting value $S_S$ only has one enhancing component. In this case, the reconstruction unit 440 multiplies each intrinsic characteristic signal in the first group by the single enhancing component.

Figure 5:
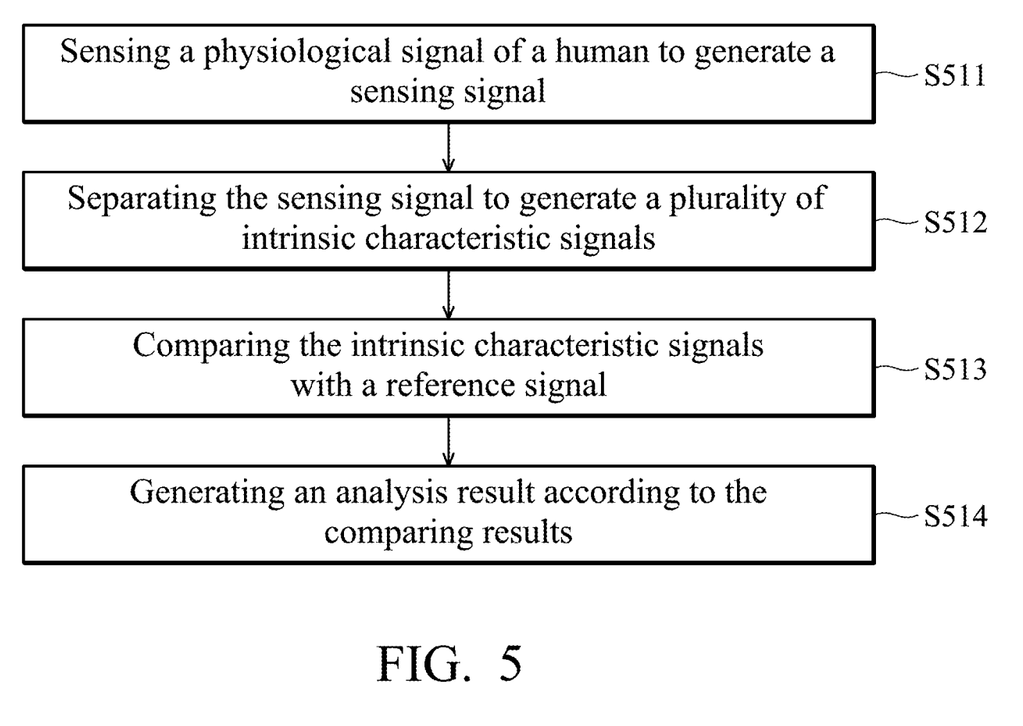
FIG. 5 is a flowchart of an exemplary embodiment of an analysis method, in accordance with an embodiment of the invention.

FIG. 5 is a flowchart of an exemplary embodiment of an analysis method, in accordance with an embodiment of the invention. The analysis method is utilized to analyze the physiological signal of a human and generate an analysis result. A user is capable of determining the physiological condition of the human according to the analysis result. First, a physiological signal of a human is sensed to generate a sensing signal (step S511). The invention does not limit how the physiological signal is sensed. Different physiological signals are sensed by different sensing elements. In one embodiment, a force sensor, a piezoelectric sensor, an accelerator, a wearable sensor, a photoplethysmo-sensor or a flexibility sensor is utilized to execute step S511.

Then, the sensing signal is separated to generate a plurality of intrinsic characteristic signals (step S512). The invention does not limit how the sensing signal is separated. In one embodiment, an EMD method is utilized to process the sensing signal. In another embodiment, after intrinsic characteristic signals are overlapped for each other, the overlapped result is the same as the sensing signal.

The intrinsic characteristic signals are compared with a reference signal to generate a plurality of comparing results (step S513). In this embodiment, step S513 is to compare the intrinsic characteristic signals with the reference signal one by one and generate various comparing results. In one embodiment, each of the comparing results represents a similarity between a corresponding intrinsic characteristic signal with the reference signal. In some embodiments, the reference signal is also a physiological signal and sensed from the same human. In other embodiments, the reference signal interferes with the physiological signal generated by step S511. For example, the reference signal may be the degree of a shaking motion by the human. Therefore, step S511 further senses an event to generate the reference signal, wherein the physiological signal generated by step S511 or the sensing signal is interfered with by the event.

The intrinsic characteristic signals are divided into a first group and a second group according to the comparing results and then an analysis result is generated according to the intrinsic characteristic signals of the first group (step S514). In this embodiment, each of the first and second groups has at least one intrinsic characteristic signal. The invention does not limit how step S514 divides the intrinsic characteristic signals. In one embodiment, step S514 classifies the intrinsic characteristic signals into the first or second group according to the similarity between each of the intrinsic characteristic signals and the reference signal.

For example, when the similarity between a first intrinsic characteristic signal among the intrinsic characteristic signals and the reference signal is higher than a pre-determined value, the first intrinsic characteristic signal is classified into the second group. When the similarity between a second intrinsic characteristic signal among the intrinsic characteristic signals and the reference signal is lower than the pre-determined value, the second intrinsic characteristic signal is classified into the first group.

In another embodiment, step S514 divides at least one intrinsic characteristic signal into the second group according to a setting value. In other embodiments, step S514 enhances each of intrinsic characteristic signals in the first group to generate a plurality of enhancing signals according to a setting value and then generates the analysis result according to the enhancing signals. Therefore, characteristic waves are enhanced. In an embodiment, the setting value has a plurality of enhancing components. Each enhancing component corresponds to one intrinsic characteristic signal in the first group. In another embodiment, a first component among the enhancing components is different from a second component among the enhancing components. Therefore, the enhancing degree of one intrinsic characteristic signal in the first group may be the same or different from that of another intrinsic characteristic signal in the first group.

Additionally, the invention does not limit how step S514 generates the analysis result. In one embodiment, step S514 is to reconstruct intrinsic characteristic signals in the first group. In another embodiment, one intrinsic characteristic signal in the first group serves as the analysis result in step S514 according to a setting value. In addition, since the analysis result generated by step S514 does not relate to the intrinsic characteristic signals in the second group, the analysis result does not have a component interfered by an event which may be excessive breathing or shaking by the human.

Since the physiological conditions of a human are generally non-stable and non-linear conditions, when the physiological signal of the human is sensed, an event interfering with the physiological signal is also detected. The interfered component is removed from the sensed physiological signal to obtain a correct analysis result to help monitor physiological readings for a long time. The event may be excessive breathing or shaking by the human.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

While the invention has been described by way of example and in terms of the preferred embodiments, it is to be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An analysis process device processing a first physiological signal to generate an analysis result and comprising:
   a detector configured to detect the first physiological signal to generate a sensing signal and a second physiological signal to generate a reference signal;
   a separation unit configured to separate the sensing signal to generate a plurality of intrinsic characteristic signals;
   a comparing unit configured to compare each of the intrinsic characteristic signals with the reference signal and generating a plurality of comparing results; and
   a reconstruction unit configured to divide the intrinsic characteristic signals into a first group and a second group according to the comparing results and generate the analysis result according to the intrinsic characteristic signals of the first group, wherein the detector detects the first physiological signal and the second physiological signal simultaneously, and wherein the intrinsic characteristic signals of the first group are not influenced by the second physiological signal, and the intrinsic characteristic signals of the second group are influenced by the second physiological signal.

2. The analysis process device as claimed in claim 1, wherein the reconstruction unit enhances the intrinsic characteristic signals of the first group to generate a plurality of enhancing signals according to a setting value and generates the analysis result according to the enhancing signals.

3. The analysis process device as claimed in claim 2, wherein the setting value has a plurality of enhancing components, each of the enhancing components corresponds to one of the intrinsic characteristic signals of the first group, and a first component among the enhancing components is different from a second component among the enhancing components.

4. The analysis process device as claimed in claim 1, wherein each of the comparing results means a similarity between a corresponding intrinsic characteristic signal among the intrinsic characteristic signals and the reference signal.

5. The analysis process device as claimed in claim 4, wherein when the similarity between a first intrinsic characteristic signal among the intrinsic characteristic signals and the reference signal is higher than a pre-determined value, the reconstruction unit classifies the first intrinsic characteristic signal to the second group.

6. The analysis process device as claimed in claim 1, wherein the separation unit utilizes an empirical mode decomposition method to process the sensing signal.

7. The analysis process device as claimed in claim 1, wherein when the intrinsic characteristic signals are overlapped to generate an overlap result, the overlap result is the same as the sensing signal.

8. The analysis process device as claimed in claim 1, wherein the sensing unit detects an event to generate the reference signal, and the sensing signal is influenced by the event.

9. The analysis process device as claimed in claim 1, wherein the sensing unit is a force sensor, a piezoelectric sensor, an accelerator, a wearable sensor, a photoplethysmosensor or a flexibility sensor.

10. The analysis process device as claimed in claim 1, wherein the reconstruction unit converts similarities between the intrinsic characteristic signals of the first group and the reference signal to a reconstruction matrix, generates a product by multiplying the reconstruction matrix by a setting value, and then generates the analysis result according to the product.

11. The analysis process device as claimed in claim 1, wherein the reconstruction unit provides one intrinsic characteristic signal of the first group as the analysis result.

12. An analysis method to analyze a first physiological signal and generate an analysis result, comprising:

utilizing a detector to sense the first physiological signal to generate a sensing signal and a second physiological signal to generate a reference signal;

separating the sensing signal to generate a plurality of intrinsic characteristic signals;

comparing each of the intrinsic characteristic signals with the reference signal to generate a comparing result;

dividing the intrinsic characteristic signals into a first group and a second group according to the comparing results and generating the analysis result according to the intrinsic characteristic signals of the first group, wherein the detector detects the first physiological signal and the second physiological signal simultaneously, and wherein the intrinsic characteristic signals of the first group are not influenced by the second physiological signal, and the intrinsic characteristic signals of the second group are influenced by the second physiological signal.

13. The analysis method as claimed in claim 12, wherein the step of generating the analysis result according to the intrinsic characteristic signals of the first group comprises:

enhancing the intrinsic characteristic signals of the first group to generate a plurality of enhancing signals according to a setting value and then generating the analysis result according to the enhancing signals.

14. The analysis method as claimed in claim 12, wherein the setting value has a plurality of enhancing components, each corresponding to one intrinsic characteristic signal of the first group, and a first component among the enhancing components is different from a second component among the enhancing components.

15. The analysis method as claimed in claim 12, wherein each of the comparing results means a similarity between a corresponding intrinsic characteristic signal among the intrinsic characteristic signals and the reference signal.

16. The analysis method as claimed in claim 12, wherein when the similarity between a first intrinsic characteristic signal among the intrinsic characteristic signals and the reference signal is higher than a pre-determined value, the first intrinsic characteristic signal is divided to the second group.

17. The analysis method as claimed in claim 12, wherein the step of separating the sensing signal to generate a plurality of intrinsic characteristic signals is to utilize an empirical mode decomposition method to process the sensing signal.

18. The analysis method as claimed in claim 12, wherein when the intrinsic characteristic signals are overlapped to generate an overlap result, the overlap result is the same as the sensing signal.

19. The analysis method as claimed in claim 12, wherein the step of generating the analysis result according to the intrinsic characteristic signals of the first group comprises:

converting similarities between the intrinsic characteristic signals of the first group and the reference signal to a reconstruction matrix;

generating a product by multiplying the reconstruction matrix by a setting value; and generating the analysis result according to the product.

* * * * *